US007727521B2

(12) United States Patent
Jalkanen

(10) Patent No.: US 7,727,521 B2
(45) Date of Patent: *Jun. 1, 2010

(54) METHOD OF AMELIORATING MULTI-ORGAN FAILURE RESULTING FROM ISCHEMIC REPERFUSION INJURY

(75) Inventor: Sirpa Jalkanen, Piispanristi (FI)

(73) Assignee: Faron Pharmaceuticals Oy, Turku (FI)

( * ) Notice: Subject to any disclaimer, the term of this patent is extended or adjusted under 35 U.S.C. 154(b) by 1004 days.

This patent is subject to a terminal disclaimer.

(21) Appl. No.: 11/242,937

(22) Filed: Oct. 5, 2005

(65) Prior Publication Data

US 2006/0034801 A1 Feb. 16, 2006

Related U.S. Application Data

(63) Continuation-in-part of application No. 10/546,653, filed as application No. PCT/FI2004/000158 on Mar. 19, 2004, now Pat. No. 7,534,423.

(60) Provisional application No. 60/515,425, filed on Oct. 30, 2003.

(30) Foreign Application Priority Data

Mar. 28, 2003 (FI) ................................. 20030467

(51) Int. Cl.
   A61K 38/21 (2006.01)
(52) U.S. Cl. ...................... 424/85.6; 530/351
(58) Field of Classification Search .................. None
   See application file for complete search history.

(56) References Cited

U.S. PATENT DOCUMENTS

| 2003/0053985 A1 | 3/2003 | Shachar et al. |
| 2006/0034801 A1 | 2/2006 | Jalkanen |
| 2006/0198821 A1 | 9/2006 | Jalkanen |

FOREIGN PATENT DOCUMENTS

| EP | 0 536 520 A1 | 4/1993 |
| EP | 0536520 A1 | 4/1993 |
| WO | WO 98/33517 A1 | 8/1998 |
| WO | WO 01/23006 A1 | 4/2001 |
| WO | 02080953 A2 | 10/2002 |
| WO | WO 02/080953 A2 | 10/2002 |
| WO | 02089828 A2 | 11/2002 |
| WO | 03075944 A2 | 9/2003 |
| WO | 2004084933 A1 | 10/2004 |

OTHER PUBLICATIONS

Mahanty S, et al. Pathogenesis of filoviral haemorrhagic fevers. The Lancet. 2004. vol. 4, p. 487-498.*
de Groot K, et al. Wegener's granulomatosis: disease course, assement of activity and extent and treatment. Lupus. vol. 7, p. 285-291.*
Herrera JL. Management of acute liver failure. Digestive Diseases. 1998. vol. 16(5), p. 274-283.*

Kiss J, et al. IFN-b protects from vascular leakage via up-regulation of CD73. Eur. J. Immunol. 2007. vol. 37, p. 3334-3338.*
Linden J. Molecular approach to adenosine receptors: receptor-mediated mechanisms of tissue protection. Annu. Rev. Toxicol. 2001. vol. 41, p. 775-787.*
Lasley RD, et al. Protective effects of adenosine in the reversibly injured heart. Ann. Thorac. Surg. 1995, vol. 60, p. 843-846.*
Panigrahi M, et al. a-Lipoic acid protects against reperfusion injury following cerebral ischemia in rats. Brain Research, 1996, vol. 717, p. 184-188.*
Poggetti, R.S. et al. Liver injury is a reversible neutrophil-mediated event following gut ischemia. Arch. Surg., 1992, vol. 127, p. 175-179.*
Veldhuis, W. et al., "Interferon-Beta Blocks Infiltration of Inflammatory Cells and Reduces Infarct Volume After Ischemic Stroke in the Rat," Journal of Cerebral Blood Flow & Metabolism, vol. 23, pp. 1029-1039, 2003 The International Society for Cerebral Blood Flow and Metabolism.
Veldhuis, W. et al., "Interferon-Beta Prevents Cytokine-Induced Neutrophil Infiltration and Attenuates Blood-Brain Barrier Disruption," Journal of Cerebral Blood Flow & Metabolism, vol. 23, pp. 1060-1069, 2003 The International Society for Cerebral Blood Flow and Metabolism.
Liu, H. et al., "Interferon-B Administration Confers a Beneficial Outcome in a Rabbit Model of Thromboembolic Cerebral Ischemia," Neuroscience Letters, vol. 327 (2002), pp. 146-148.
Ferro, J. et al., "Other Neuroprotective Therapies on Trial in Acute Stroke," Cerebrovascular Diseases 2006, vol. 21 (suppl 2), pp. 127-130.
Maier, C. et al., "Interferon-B Fails to Protect in a Model of Transient Focal Stroke," Stroke 2006, vol. 37, pp. 1116-1119.
A. O. Shakil, "A Pilot Study of Interferon Alfa and Ribavirin Combination in Liver Transplant Recipients With Recurrent Hepatitis C", Hepatology, vol. 36, 2002, pp. 1253-1258.
E. Nemoto, et al., "Expression of CD73/ecto-5'-nucleotidase on human gingival fibroblasts and contribution to the inhibition of interleukin-1 α-induced granulocyte-macrophase colony stimulating factor production", Journal of Periodontal Reseach, vol. 39, 2004, pp. 10-19.
G. Kocić, et al., "Different responses of rat liver adenosine metabolizing enzymes during in vivo and in vitro treatment with interferon-α2b", Journal of Viral Hepatitis, vol. 5, 1998, pp. 353-356.
H. Liu, et al., "Interferon-β administration confers a beneficial outcome in a rabbit model of thromboembolic cerebral ischemia", Neuroscience Letters, vol. 327, 2002, pp. 146-148.
J. Niemelä, et al., "IFN-α Induced Adenosine Production on the Endothelium: A Mechanism Mediated by CD73 (Ecto-5'Nucleotidase) Up-Regulation", The Journal of Immunology, vol. 172, 2004, pp. 1646-1653.

(Continued)

Primary Examiner—Robert Landsman
Assistant Examiner—Bruce D Hissong
(74) Attorney, Agent, or Firm—Rothwell, Figg, Ernst & Manbeck p.c.

(57) ABSTRACT

This invention relates to a method for prevention or treatment of ischemia reperfusion injury or multi-organ failure in an individual by administering to said individual an effective amount of an interferon beta.

6 Claims, 2 Drawing Sheets

OTHER PUBLICATIONS

K. Kalsi, et al., "Regulation of ecto-5'-nucleotidase by TNF-α in human endothelial cells," Molecular and Cellular Biochemistry, vol. 232, 2002, pp. 113-119.

L.D. Christensen, "Effects of Immunomodulators on Ecto-5'-Nucleotidase Activity on Blood Mononuclear Cells in Vitro," Scand. J. Immunol., vol. 35, 1992, pp. 407-413.

J. A. Elias, et al., "Transgenic modeling of interleukin-13 in the lung," *Chest*, The Cardiopulmonary and Critical Care Journal, vol. 123, No. 3, Mar. 3, 2003, pp. 339S-345S.

V. Savic, et al., "Induction of ecto-5'-nucleotidase of rat cultured mesangial cells by interleukin-1β and tumour necrosis factor-α", Immunology 1990, vol. 70, pp. 321-326.

* cited by examiner

METHOD OF AMELIORATING MULTI-ORGAN FAILURE RESULTING FROM ISCHEMIC REPERFUSION INJURY

CROSS-REFERENCE TO RELATED APPLICATION

The present application is a continuation-in-part application of U.S. patent application Ser. No. 10/546,653, filed on 24 Aug. 2005 which is a national stage filing under 35 U.S.C. §371 of International patent application No. PCT/FI2004/000158, filed on 19 Mar. 2004 which in turn is a non-provisional of U.S. provisional patent application Ser. No. 60/515,425, filed 30 Oct. 2003, from which priority is claimed under 35 U.S.C. §119(e). Each of the foregoing applications is incorporated herein by reference. International patent application No. PCT/FI2004/000158 also claims priority to Finland patent application No. 20030467 filed on 28 Mar. 2003.

BACKGROUND OF THE INVENTION

This invention relates to a method for prevention or treatment of ischemia reperfusion injury or multi-organ failure in an individual by administering to said individual an effective amount of an interferon beta.

The publications and other materials used herein to illuminate the background of the invention, and in particular, cases to provide additional details respecting the practice, are incorporated by reference.

Several conditions, including abdominal injuries, bowel infraction, cardiovascular surgery and shock, can lead to intestinal ischemia-reperfusion injury (IRI). Importantly, besides causing local injury IRI also triggers systemic inflammatory response in remote organs resulting in a syndrome called multi-organ failure. In this syndrome lungs are especially vulnerable. The most prominent signs of the injury are increased vascular permeability (vascular leakiness) and neutrophil accumulation. The lung injury subsequent to intestinal IRI is primarily due to release of pro-inflammatory cytokines in the gut. Intestinal IRI increases intestinal permeability with subsequent release of bacterial endotoxin that promotes systemic inflammation in multi-organ failure. Also other mediators released from activated neutrophils play an important role.

CD73 (ecto-5'-nucleotidase, 5'-NT) is a glycoprotein expressed on the surface of lymphocytes and endothelial and epithelial cells. CD73 regulates leukocyte adhesion via its enzymatic function. It catalyzes hydrolysis of AMP to adenosine. Adenosine produced by CD73 decreases vascular permeability and neutrophil sequestration in hypoxic tissue. However, the role of CD73 in distant organ injury in IRI is not known.

Due to the central role of vascular leakage in IRI, molecules regulating the permeability changes via adenosine or by other mechanisms may be potential targets to combat multi-organ failure. Since interferon beta is known to both induce CD73 expression (and adenosine production) and has other immunomodulatory effects, we studied its utility in distant organ injury in multi-organ failure.

SUMMARY OF THE INVENTION

Thus, this invention concerns a method for prevention or treatment of a disease selected from the group consisting of ischemia reperfusion injury and multi-organ failure in an individual by administering to said individual an effective amount of an interferon beta.

DETAILED DESCRIPTION OF THE INVENTION

Figure 1:
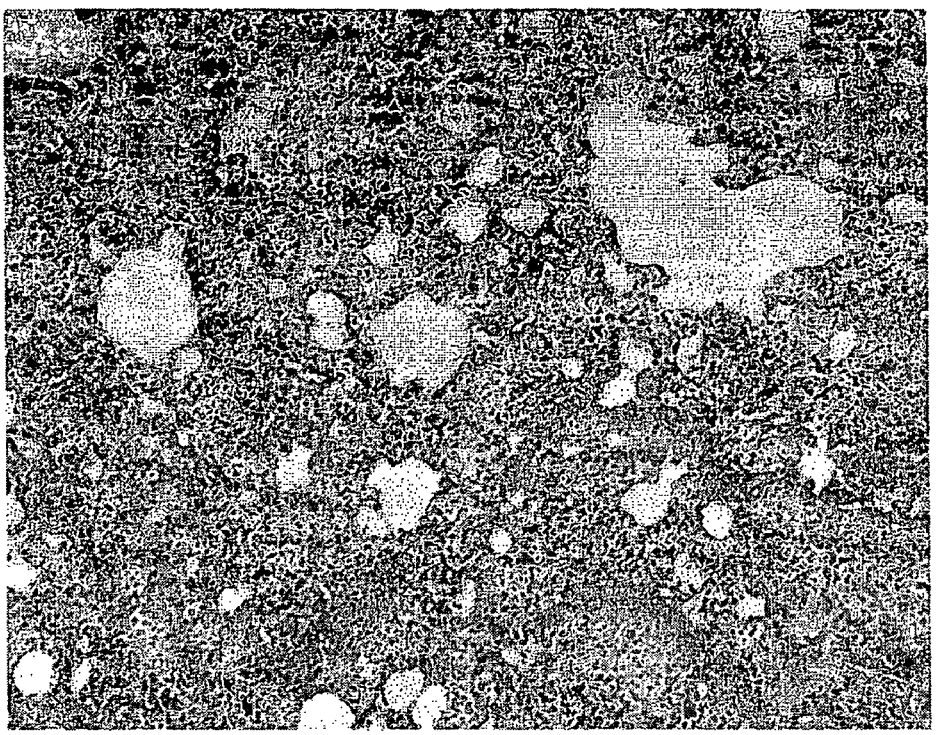
FIG. 1 shows Hematoxylin-eosin stainings of formalin-fixed paraffin-embedded sections of lungs of the rats with multiorgan failure without treatment (A) or with IFN-beta and AMP treatment (B).
Figure 1:
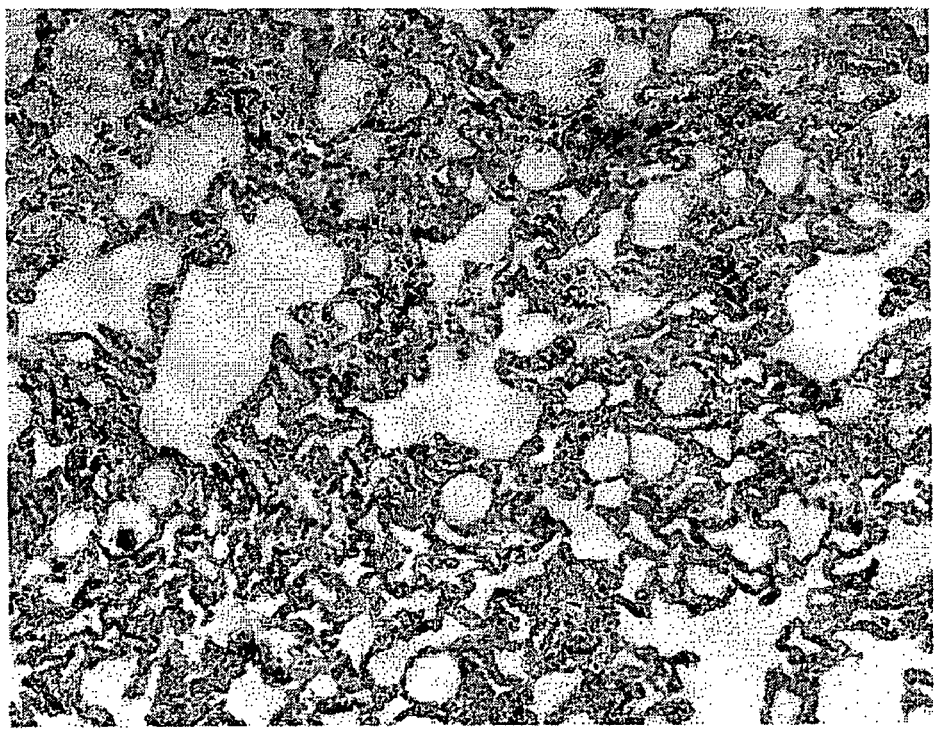

Definitions and preferable embodiments:

The term "treatment" or "treating" shall be understood to include complete curing of a disease as well as amelioration or alleviation of said disease.

The term "interferon beta" shall be understood to include any interferon beta. Thus, it shall cover any subtype thereof, such as interferon beta 1a, interferon beta 1b, etc., and mixtures thereof.

The term "prevention" shall be understood to include complete prevention, prophylaxis, as well as lowering the individual's risk of falling ill with said disease. This term shall also be understood to include preconditioning of tissue by administering an interferon beta according to the method of this invention at a very early stage (e.g. before operations, before complete diagnosis at stroke and infarct patients) so as to prevent the tissue from damages.

The term "individual" refers to a human or animal subject.

The expression "effective amount" is meant to include any amount of an agent according to the present invention that is sufficient to bring about a desired therapeutical result, especially upon administration to an animal or human subject.

Although it is likely that the therapeutic effect of interferon beta is mediated by an elevation of the adenosine level, optionally due to increased expression of CD73, followed upon administrating of interferon beta, it should be stressed that also other alternative mechanisms could be involved, especially in multi-organ failure. Therefore, the effect of interferon beta shall in its broadest meaning be understood not to be restricted to any particular mechanism of action.

The wording "elevated level of adenosine" shall be interpreted as an adenosine level that is at least 2% higher, preferably at least 20% higher, most preferably at least 30% higher than the normal tissue level would be without the measures taken according to this invention.

In situations where the mechanism of action is mediated via elevation of the adenosine level, the administration of interferon beta is preferably combined with an administration of adenosine monophosphate (AMP) in order to safeguard the source for adenosine to be produced as result of the elevated CD73 level, obtained by elevated expression induced by interferon beta.

According to another preferable embodiment, the administration of interferon beta is combined with an administration of an adenylate kinase inhibitor, which prevents AMP from conversion into adenosine diphosphate (ADP) or adenosine triphosphate (ATP). A combined administration of interferon beta with AMP and such an adenylate kinase inhibitor may be particularly preferred.

According to still another preferred embodiments, the administration of interferon beta is combined with an administration of an adenosine deaminase inhibitor which prevents the decomposition of adenosine. This could also further be combined with administration of AMP and optionally also an adenylate kinase inhibitor which prevents AMP from conversion into adenosine diphosphate (ADP) or adenosine triphosphate (ATP).

Figure 2:
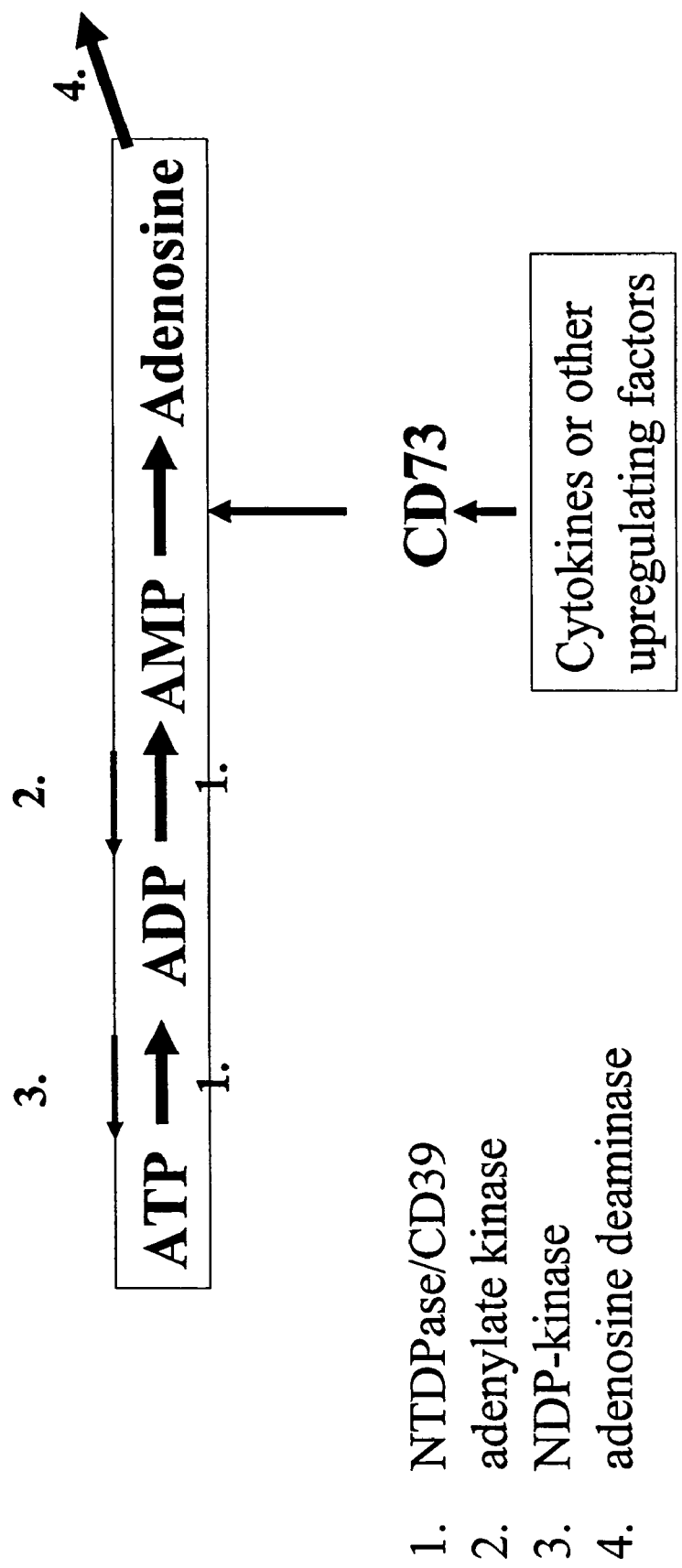
FIG. 2 shows metabolic pathways regulating adenosine levels. The enzymatic reactions leading to the formation and degradation of adenosine are depicted. The amount of adenosine can be elevated by 1. upregulating/increasing amount of CD73; 2. providing more AMP; 3. inhibiting adenylate kinase, and 4. inhibiting adenosine deaminase, or combinations thereof.

The metabolic pathways regulating adenosine levels are shown in FIG. 2.

According to another preferable embodiment, the administration of interferon beta, optionally in combination with administration of adenosine monophosphate, is started as soon as a trauma patient or infarction or stroke patient is brought to care, optionally even if the final diagnosis is not fully clarified. Hereby the adenosine level can be increased as rapidly as possible. In case of surgical operations it may be useful to start administering of interferon beta, optionally in combination with administration of adenosine monophosphate, already before the operation, for example 12 h before the start of the operation. Also in these cases an adenylate kinase inhibitor and/or an adenosine deaminase inhibitor could be administrated in addition to the agents mentioned above.

Therapeutically effective amounts, administration routes and dosage forms:

The therapeutically effective amount of the interferon beta according to this invention to be given to a patient in need of such treatment may depend upon a number of factors including, for example, the age and weight of the patient, the precise condition requiring treatment and its severity, and the route of administration. The precise amount will ultimately be at the discretion of the attending physician. Thus, practice of the present invention may involve any dose, combination with other therapeutically effective drugs, pharmaceutical formulation or delivery system for oral, topical, inhalation or parenteral administration.

Amounts and regimens for the administration of the agents according to the present invention can be determined readily by those with ordinary skill in the art of treating inflammation-related disorders, such as reperfusion injuries, stroke, organ transplantation, traumas, or multi-organ failure syndrome.

Based on this invention it can be assumed that e.g. subcutaneously, intramuscularly, intravenously or transdermally given interferon beta will increase local concentration of adenosine, which is anti-inflammatory. This overcomes the problems related to the use of adenosine, which has a very short half-life and is therefore, not optimal for therapeutic use.

The interferon beta may according to the present invention preferably be administered by infusion or by injection. Intravascular infusions are normally carried out using parenteral solutions contained within an infusion bag or bottle, and may be connected to different systems to control the rate of administration of the parenteral solution. The interferon beta may according to the present invention alternatively be administered as an aerosol.

Preferred formulations for infusion or injection may include carriers, such as human serum albumin, pharmaceutically acceptable salts, buffers, such as phosphates and/or other pharmaceutically acceptable excipients. The active ingredient, the interferon beta may be provided in amounts ranging from e.g., $1\text{-}50 \times 10^6$ IU per ml. The formulation may preferably be provided as lyophilised powder in dosage form, to be prepared by the addition of water or other solutions suitable for injection prior to the administration.

Interferon beta can be given to the patients suffering from or being at risk of getting inflammations. Those types of inflammatory conditions are for example ischemia reperfusion injuries during the stroke and myocardial infarction. Also organ transplantation and trauma are occasions often associated with major inflammatory components.

The adenosine monophosphate (AMP) may be administered e.g. subcutaneously, intramuscularly, intravenously or transdermally. A typical daily dose may be in the range 0.1 to 100 mg/kg body weight.

Also an optionally used adenylate kinase inhibitor or an adenosine deaminase inhibitor may be, for example, administered subcutaneously, intramuscularly, intravenously or transdermally. A typical daily dose of such inhibitors may be in the range 0.1 to 100 mg/kg body weight.

The invention will be illuminated by the following non-restrictive Examples.

EXAMPLE 1

Treatment of Mice with IFN-beta in Multi-Organ Failure

Weight-, sex- and age-matched C57Black mice were used in this study.

Preoperative treatment and surgical procedure

Mice were treated on three conceqvtive days before the induction of the multi-organ failure with subcutaneous injections of interferon-beta (6000 IU/dose) or PBS. For the operation, the mice were anesthesized with ketamine hydrochloride (100 mg/kg of body weight, IP) and xylazine (10 mg/kg of body weight, IP). Superior mesenteric artery was dissected via laparotomy and occluded by microvascular clamp for 30 minutes. During the procedure total of 2 ml of sterile saline was subcutaneously injected into the mice to compensate for the fluid loss by evaporation. The microvascular clamp was released after the ischemia period. Animals were sacrificed after 4 hours of reperfusion and tissue samples were collected.

Analysis of Vascular Leakage in the Lungs

Mice received intravenously fluorescein-conjugated dextran (molecular weight 70 kDa, 25 mg/kg of body weight in 0,2 ml of sterile saline) 5 minutes prior to sacrifice. This fluorescent dye does not leak out from intact vessels. 7 micrometer cryo-sections were cut from lung tissue samples and examined in a fluorescent microscope. Intensity of tissue fluorescence exceeding a pre-set threshold and area of leakiness was calculated from the images collected by digital camera at x 200 magnification using Image J computer software.

Results

In control treated mice FITC-dextran was detected outside the vessels as an indication of vascular damage and leakiness of the endothelial cell barrier. In contrast, no leakiness outside the vasculature was seen in mice treated with interferon-beta. Table 1 summarizes the results when counted as an area of leakiness and Table 2 as an intensity of fluorescence above the pre-set threshold value. Thus, interferon beta treatment protects the animals from the adverse effects of multi-organ failure in lungs. These data show that interferon beta treatment is useful as a profylaxis in conditions predisposing to multi-organ failure (surgery, injury) and it may be useful for treatment of multi-organ failure in an already ongoing disease.

TABLE 1

| | Leakage area | | |
|---|---|---|---|
| IFN-beta treatment | − (n = 13) | + (n = 8) | |
| Mean ± SEM | 9 ± 2.5%[a] | 0.0 ± 0.0% | P < 0.0001 |

[a] % of total area

TABLE 2

| | Fluorescence intensity | | |
|---|---|---|---|
| IFN-beta treatment | − (n = 13) | + (n = 8) | |
| Mean ± SEM | 26.77 ± 4.91[a] | 2.03 ± 1.27 | P < 0.0001 |

[a] Mean fluorescence intensity

EXAMPLE 2

Combined Treatment of Rats with AMP and IFN-beta in Multi-Organ Failure

Model: The multiorgan failure was induced to rats (weight: 250 g) by clamping the mesenteric artery for 30 minutes. Thereafter, the reperfusion time was two hours. The rats in the treatment group were injected sybcutaneously with 10 000 units of IFN-beta 18-20 hours before the clamping of the artery. Throughout the actual experiment the animals received 37.5 mg AMP in 3 ml saline as a continuous intravenous infusion. Rats with induced multiorgan failure but without treatment served as controls. At the end of the experiment, the histology of the lungs, which is one of the major target organs in this experimental model was analyzed.

Results: Lungs of the control rats without treatment showed collapsed alveolar space as can bee seen in FIG. 1(A), whereas rats which received IFN-beta and AMP did not show marked collapsing of the alveolar space (FIG. 1B). Thus, treatment with IFN-beta and AMP protects from the complications of multiorgan failure.

Overall these results suggest that interferon beta may be a relevant in vivo regulator of CD73 in the endothelial-leukocyte microenvironment and thus have a fundamental role in controlling the extent of inflammation via CD73-dependent adenosine production.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method of ameliorating multi-organ failure resulting from ischemic reperfusion injury in an individual in need thereof comprising administering a therapeutically effective amount of interferon beta to the individual in need thereof.

2. The method according to claim 1 wherein the ameliorating effect of said interferon beta is mediated via elevation of the adenosine level in the individual.

3. The method according to claim 2 wherein the elevation of the adenosine level is induced by enhanced CD73 expression.

4. The method according to claim 2 wherein an effective amount of adenosine monophosphate is administered to the individual.

5. The method according to claim 2 wherein an adenylate kinase inhibitor, which prevents AMP from conversion into adenosine diphosphate (ADP) or adenosine triphosphate (ATP) is administered.

6. The method according to claim 2 wherein an adenosine deaminase inhibitor which prevents the decomposition of adenosine, is administered.

* * * * *